May 2, 1972 H. W. MOTZKAU Plant Pat. 3,143
AZALEA PLANT
Filed Aug. 26, 1970
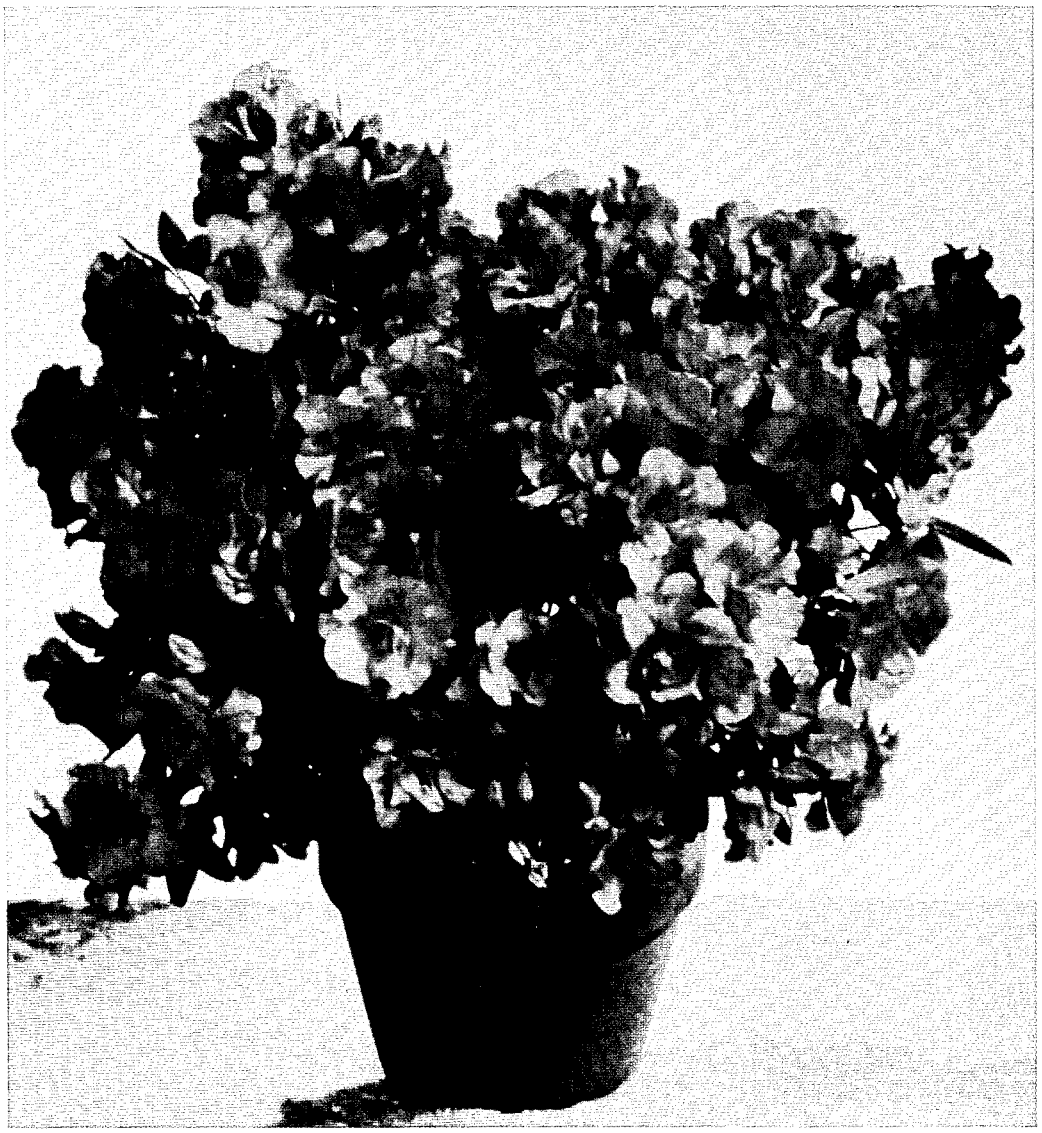
INVENTOR
HENRY W. MOTZKAU
BY
Oberlin, Maky, Donnelly & Renner
ATTORNEYS United States Patent Office Plant Pat. 3,143
Patented May 2, 1972

3,143
AZALEA PLANT

Henry W. Motzkau, Whitewater, Wis., assignor to Yoder Brothers, Inc., Barberton, Ohio Filed Aug. 26, 1970, Ser. No. 67,299
Int. Cl. A01h 5/00
U.S. Cl. Plt.—57 1 Claim The present invention comprises a new and distinct variety of azalea plant which has resulted from crossing certain azalea selections in a program of controlled hybridization. The seed parent is unnamed and unpatented, and identified for breeding purposes as seedling #536. The pollen parent is the unpatented variety, Cascade.

The new variety is similar in many respects to the variety Anytime, U.S. Plant Pat. No. 2,568, having the same characteristics as Anytime of (1) Ease of budding,
(2) Early response,
(3) Ease of rooting,
(4) Long lastingness,
(5) Evergreen type foliage.

The new variety is distinguished from Anytime by the following characteristics:

(1) Kiwi has a darker and more brilliant rose color than Anytime.

(2) Kiwi has strong peduncles; Anytime has weak, floppy peduncles.

(3) Kiwi has excellent cooler tolerance; Anytime is sensitive to leaf drop in cooler.

(4) Kiwi does not need growth regulators to produce a compact plant; Anytime generally requires growth regulators to control its wild irregular growth habit.

The new variety was selected from a progeny of seedlings from the above mentioned parents. Varietal worth was determined by flowering liners from the initial selection in both a year round and natural seaon developmental flowering program over a period of 5 years. Stock growth was evaluated in the vicinity of Fort Myers, Fla.

My new variety has been asexually reproduced by cuttings at Whitewater, Wis., and has been found to retain its distinctive characteristics through successive propagations.

My new variety when grown in the vicinity of Barberton, Ohio, has a response described as Early-Mid season. It will be understood that the response time and blooming period may vary significantly with varying environmental conditions such as temperature and amount of daylight. Suggested flowering period is from the first of January through April in a natural season program, and year around (all 12 months) in a controlled flowering program.

The accompanying drawing shows the unique features of my new variety, the colors being as nearly true as possible with color illustrations of this type.

The following is a detailed description of my new variety based on observations made in a greenhouse in Barberton, Ohio. Color references are to the Munsell Color Book, 1963, edition.

Botanical classification: *Rhododendron hybrida,* evergreen type.

Flower:

*Color.*—Rose (Spring color at Barberton, Ohio); general tonality—rose 7.5R5/14. Anytime—deep purplish pink—7.56/13; sepals first divide—dark medium pink, 7.5RP4/10; petals unfurl—rose pink between 8.75RP/12 and 4/14; fully open—inside petals—rose, 7.5RP5/14; reverse petals—rose, lighter than 7.5RP5/14; base of petals—coral pink, near 1.25R6/12; outer hose—petaloid calyx not a complete hose, color rose 7.5RP5/14 with streaking to coral pink; base, 1.25R6/12, with some green sectors; variations—dotted uppers, dark red near 2.5R3/10. (Anytime—strong purplish red, 10RT4/12); discoloration—retains color approximately 3 weeks, followed by gradual fading.

*Bud.*—Size—medium size; form—conoidal; opening habit—opens cup-like, retains cup-like form.

*Bloom.*—Size—medium; average—2¼", range 2"–2½". (Anytime is 3" to 3½"); borne—several together; average 3; range 1–4; form—semi-double, with varying degrees of petaloid anthers; Calyx petaloid but not complete hose. (Anytime is recorded as double.)

*Blooming habit.*—Once, profusely; response—natural season, early-mid season. Christmas flowerings generally possible for northern areas of the United States. Year round—early. Sets buds easily under a wide range of environmental conditions.

*Sepals.*—Normal, smooth, somewhat hairy, fall off as flowers open.

*Peduncle.*—Length—short; aspect, hairy; strength, strong.

*Petals.*—Texture—soft; appearance—inside, satiny; outside, satiny; form—rounded, notched terminal; arrangement—imbricate with petaloids; fragrance—none; persistence—hang on and dry; non-shatter; longevity—greenhouse, 2–3 weeks; home, 3–4 weeks.

*Reproductive organs.*—Stamen, anthers—5–10. Variable; most are petaloid, tannish rose, 10RP5/10; filaments—thin, almost smooth, pink, 7.5RP6/12; style—generally columnar, may be fasciated, pink, 10RP5/12; stigmas—generally normal, may be fasciated, tannish pink, near 5R5/6; ovaries—hypogynous.

Plant: Bush, rounded formal plant.

*Growth habit.*—Compact; rounded.

*Breaking habit.*—Excellent.

*Size.*—Of average finished product grown from the standard #7 liner of Yoder Brothers, Inc., Barberton, Ohio; height—9"–12"; diameter—10"–15".

*Rooting habit.*—Good, easy. Growth from own roots; vigorous; budding ease—excellent; uniformity of budding—excellent; growth regulator—not needed for budding.

*Foliage.*—Type—evergreen; leaflets—single; size—length, average 2"; range 1½"–2¾"; width, average 1"; range ½"–1⅛"; shape—ovate to obovate; texture—upper, somewhat glossy; lower, glossy; rib and veins—slightly depressed; edge—smooth; color—new foliage, upper, light green, 5GY5/6; lower, light green, 5GY6/6; mature foliage; upper, dark green, 7.5GY2/4; lower, green, near 10GY4/4; petiole—short, hairy, green, 5GY6/6.

*Stems.*—Color—new wood, green, 5GY6/4; mature wood, brown, near 7.5YR4/6.

*Recommended flowering period.*—Year round—all 12 months in controlled program; natural season—late December through April.

*Responsiveness to day length and temperature.*—Buds and flowers under a wide range of environmental conditions.

*Cooler tolerance.*—Excellent.

*Shipping tolerance.*—Excellent.

I claim:

1. A new and distinct variety of azalea characterized particularly as to novelty by its rapid yet compact growth habit, its rose color, its long-lasting flowers, its non-shattering, its evergreen type foliage, its early-mid season profuse flowering, and its adaptability to year round flowering programs.

No references cited.

ROBERT E. BAGWILL, Primary Examiner